United States Patent [19]

Youssef

[11] 4,329,431
[45] May 11, 1982

[54] INSTANT CULTURE MEDIA AND METHOD OF STERILIZING SAME

[76] Inventor: Kamal A. Youssef, P.O. Box 6548, West Palm Beach, Fla. 33405

[21] Appl. No.: 196,929

[22] Filed: Oct. 14, 1980

Related U.S. Application Data

[63] Continuation-in-part of Ser. No. 913,584, Jun. 8, 1978, Pat. No. 4,248,971.

[51] Int. Cl.³ .............................................. C12N 1/20
[52] U.S. Cl. ................................... 435/253; 252/399; 252/401; 252/405; 252/407; 422/28; 422/30; 422/36; 422/37; 435/243; 435/254; 435/255; 435/256; 435/800
[58] Field of Search ............... 435/243, 253, 254, 255, 435/256, 800; 252/399, 401, 405, 407; 422/28, 30, 34, 36, 37

[56] References Cited

U.S. PATENT DOCUMENTS

| | | | |
|---|---|---|---|
| 620,022 | 2/1899 | Effront | 435/93 |
| 2,189,949 | 2/1940 | Griffith et al. | 422/35 X |
| 3,041,250 | 6/1962 | Wolnak et al. | 435/144 X |
| 3,293,145 | 12/1966 | Leavitt et al. | 435/244 |
| 4,040,977 | 8/1977 | Eggensperger et al. | 422/36 X |
| 4,248,971 | 2/1981 | Youssef | 435/253 |

FOREIGN PATENT DOCUMENTS 266414 2/1927 United Kingdom ................ 435/800

*Primary Examiner*—Robert J. Warden
*Attorney, Agent, or Firm*—Albert F. Kronman

[57] ABSTRACT

Disclosed are culture media comprising a gelling agent, germicidal bleach containing a halogen, a halogen-inactivating agent to inactivate residual halogen and conventional nutrients.

Also disclosed is a method for sterilizing a culture medium without autoclaving same by dissolving a gelling agent in buffered water; adding thereto a germicidal bleach containing a halogen; thereby forming a suspension; heating the suspension to boiling; adding to the stirred and heated suspension an excess of halogen-inactivating agent to neutralize residual halogen and then adding nutrients.

10 Claims, No Drawings

INSTANT CULTURE MEDIA AND METHOD OF STERILIZING SAME

REFERENCE TO CO-PENDING APPLICATION

This application is a continuation-in-part of application Ser. No. 913,584 filed June 8, 1978, and now U.S. Pat. No. 4,248,971.

FIELD OF THE INVENTION

This invention relates to an instant culture medium and to a method for sterilizing culture media without autoclaving.

BACKGROUND OF THE INVENTION

The standard routine practice in the vast majority of laboratories is to sterilize the microbiological and bacteriological culture media by the heating process called "autoclaving". Autoclaving is a form of "pressure-cooking" by which the nutrients or media are subjected to "trapped" or pressurized steam in a sturdy vessel "autoclave" or "pressure cooker" usually under a pressure of 15 lb/square inch to produce a temperature of approximately 121° C. for about 20 minutes. Exposure of the medium to this "superheated steam" ensures or guarantees the destruction or annihilation of all forms of life: vegetative and otherwise (e.g. heat-resistant spores). The drawbacks or disadvantages of this widely used method of sterilizing culture media include:
1. Caramelization.
2. pH Changes.
3. Protein disintegration, denaturation and/or breakdown.
4. Inactivation of certain vitamins and growth-promoting factors.
5. Clouding and adverse effects on the optical clarity of the medium.
6. Possible undesirable physical and/or chemical actions and interactions that may take place by and among the different ingredients of the medium.
7. Agar agar hydrolysis.
8. Frequency of failures, errors, hazards and accidents related to heat sterilization equipment, i.e. the autoclave.
9. Time consuming.

There is accordingly a need for a culture medium which will obviate the aforementioned drawbacks of the prior art and which will have a long shelf life.

The main object of this invention is to provide such a medium.

SUMMARY OF THE INVENTION

Culture media in accordance with the present invention comprise in weight percent:

about 0.0% to 5% of a gelling agent;
about 0.015% to 0.03% of a bleaching agent having germicidal and biocidal properties and containing at least one halogen or halogen-liberating compound capable of providing a final halogen concentration in water of about 50 to about 100 parts per million; it must be compatible with the gelling agent if one is used; about 0.22 to 0.06% of a halogen-inactivating agent having at least one thio, mercapto, or sulfhydril group; about 7% to 50% of a sterilized or presterilized nutrient concentration, preferably, cold concentrated nutrients; the balance water preferably distilled or demineralized water.

More specifically, the media comprises the following components: "A"—Agar agar: or one or more similar gelling agents such as Carrageenan, pectin, silicone gel, guar gum, locust bean gum, corn starch, alginic acid, kelp, and various gellable polysaccharides. "B"—Bleach: comprises one or more of several halogens and halogen-liberating compounds, usually in dry powder form, for a final halogen concentration, in aqueous concentration of 50-100 ppm (parts per million). Examples of these compound/s are: chlorine, iodine & bromine, as such, and/or their derivatives both organic and inorganic. Typical examples are: 5% sodium hypochlorite (liquid), lithium hypochlorite, and calcium hypochlorite ("bleaching powder"). Typical examples of organic derivatives are: chlorinated isocyanurates such as the sodium or potassium salts of dichloro-s-triazinetrione; halogenated hydantoins such as N-bromo-N-chloro-5,5-dimethylhydantoin and 1,3-dichloro-5,5,-dimethylhydantoin "Halane"; p-(N,N-dichlorosulfamyl) benzoic acid "Halazone"; trichloro-s-triazine-trione and trichloroisocyanuric acid and mixtures thereof. These compounds have good biocidal properties and sufficient water solubility. Hypobromites, interhalogens such as bromine chloride, iodine chloride, and iodine bromide also are operative. Also useful are quaternary ammonium halides commonly called "Quats", for example, benzalkonium chloride and hyamine Quats as well. Aldehydes such as formaldehyde may also be used (1:5000–1:10000) as well as its derivatives: formalin and paraformaldehyde. "N"-Halogen-inactivation agents: these include sodium bisulfite, alkali meta persulfates and sodium thiosulfate, sodium thioglycollate and other compounds bearing thio, mercapto or sulfhydril group. These are used in 1½ to 2 times the amount of halogen compound. This figure represents an excess which ensures complete and irreversible inactivation of the active residual halogen. In case of aldehydes i.e. formaldehyde an oxidizing agent such as potassium persulfate, "Oxone" brand by Dupont will inactivate the aldehyde. "C"—Concentrate. The nutrients used are any of the conventional materials in 10 to 20 times the normal concentration in the particular culture medium. This concentrate is sterilized or pre-sterilized by microfiltration or other conventional method. It should be noted that certain nutrients are available in a naturally sterile condition and do not require sterilization, such as those in appropriate concentrations in alcohol or in chloroform.

The present invention also provides a method for forming and sterilizing a culture medium which method comprises; providing in a culture medium container at least one water soluble biocidal and germicidal agent containing at least one halogen or halogen-liberating compound capable of providing a final halogen concentration in water of about 50 to 100 parts per million; adding a halogen-inactivating agent in an amount sufficient to inactivate or neutralize any residual halogen and then adding a sterilized concentrated solution containing conventional nutrients. After addition of the nutrients, a sterile enrichment can be added and the solution then poured into sterile containers. In a modification of the invention, an aldehyde such as formaldehyde or its derivative paraformaldehyde is used as the germicidal agent with an oxidizing agent serving as the neutralizing or inactivating agent such as an alkali metal persulfate in the presence of appropriate buffering salts.

DISCLOSURE

The invention is further illustrated in non-limiting fashion by the following examples.

EXAMPLE I

This medium contains: (in grams per liter)

| | | |
|---|---|---|
| "A": Bacteriological agar agar | 15 | gm |
| Sodium Chloride | 5 | gm |
| Buffering salts (pH 7.4) | 3 | gm |
| "B": Pure sodium dichloro-s-triazinetrione dihydrate | 0.2 | gm |
| "N": Sterile 10% solution of sodium thiosulfate | 5 | c.c. |
| "C": Enzymatic casein digest | 15 | gm |
| Enzymatic soybean meal digest | 5 | gm |
| Distilled water | 50 | c.c. |

The medium is prepared as follows: In a clean and dry 2-liter Erlenmeyer's flask (Flask #1) empty contents of package "B" (above). Add 950 c.c. of distilled water to the flask. Stopper the flask with screw cap or neoprene rubber stopper. Dissolve the compound completely and uniformly by shaking the flask vigorously. Set or put the flask aside momentarily. In a separate dry and clean 2-liter Erlenmeyer's flask empty the contents of package "A". Measure 300-500 c.c. of dissolved halogen compound from Flask No. 1 and add gradually to "A", shaking fairly strongly meanwhile to disperse and suspend the solids in the halogenated water. Add a magnetic bar (to be used with a hot plate magnetic stirrer: "Gyrotherm" to the suspension. Heat the suspension to boiling with continuous mixing either directly on the flame or by using the hot plate (Gyrotherm) for 2-3 minutes. Add the balance of the chlorinated water from Flask #1 to the melted agar solution maintaining a mixing action by the magnetic bar. Add 5 c.c. of "N" (10% sodium thiosulfate solution) while the mixing action by the magnetic bar is maintained. With sterile precautions, add "C" while the magnetic stirring action is still maintained. The medium is now ready for dispensing or "pouring" into sterile containers to solidify. Or, a sterile enrichment (sterile sheep or horse blood) is added while the stirring action is maintained. The product, a blood agar, now ready to "pour" into sterile containers as desired.

EXAMPLE II

Proceeding as in Example I, there is prepared an instant Mueller-Hinton medium for antibiotic sensitivity tests by the Kirby Bauer Method to make 1000 c.c. of medium mix:

| Packet "A" | |
|---|---|
| Agar agar | 15.00 Gram |
| Sodium chloride | 5.00 Gram |
| Buffering salt (pH 7.4) | 3.00 Gram |
| Starch | 1.50 Gram |

| Packet "B" | |
|---|---|
| Sodium Dichloro-s-triazinetrione dihydrate | 0.20 Gram |

| Packet "C" | |
|---|---|
| Beef infusion from | 300.00 Gram |
| Acid digested casein | 17.50 Gram |
| Distilled water | 50.00-100.00 c.c. |

| Packet "N" | |
|---|---|
| Sodium thiosulfate 10% solution (sterile) | 5.00 c.c. |

EXAMPLE III

Proceeding as in Example I, there is prepared an instant G-C medium for Gonoccus to make 1000 c.c., mix:

| Packet "A" | |
|---|---|
| Agar agar | 12.50 Gram |
| Sodium chloride | 5.00 Gram |
| Buffering salts (pH 7.4) | 3.00 Gram |
| Corn starch | 1.00 Gram |

| Packet "B" | |
|---|---|
| Sodium Dichloro-s-Triazinetrione dihydrate | 0.20 Gram |

| Packet "C" | |
|---|---|
| Peptone (meat digest) | 10.00 Gram |
| Yeast extract | 3.00 Gram |
| Liver extract | 3.00 Gram |
| Dextrose | 2.00 Gram |
| Dipotassium phosphate | 2.00 Gram |

| Packet "N" | |
|---|---|
| Sodium thiosulfate 10%-20% solution (sterile) | 5.00 c.c. |

EXAMPLE IV

By repeating the procedure of Example I there is provided a culture medium using chlorine gas in water as the sterilizing agent, sodium thiosulfate as the inactivating agent and packet "C" of Example I.

EXAMPLE V

A culture medium is prepared as in Example I using iodine in water as the sterilizing agent locust bean gum as the gelling agent, potassium thiosulfate as the inactivating agent and packet "C" of Example I.

EXAMPLE VI

A liquid culture medium is prepared as in Example I using a five percent sodium hypochlorite solution as the sterilizing agent, no gelling agent, sodium thiogylcollate as the inactivating agent and packet "C" of Example I.

EXAMPLE VII

A culture medium is prepared as in Example I using n-bromo-n-chloro-5, s-dimethyl hydantoin as the sterilizing agent, carrageenan as the gelling agent, sodium thiosulfate as the halogen-inactivating agent and packet "C" of Example I.

EXAMPLE VIII

A culture medium is prepared as in Example I using alginic acid as the gelling agent, p-(n,n-dichlorosulfamyl) benzoic acid as the sterilizing agent, sodium thiosulfate as the halogen-inactivating agent and packet "C" of Example I.

EXAMPLE IX

A culture medium is prepared as in Example I using kelp as the gelling agent, lithium hypochlorite solution as the sterilizing agent, sodium thiosulfate as the halogen-inactivating agent and packet "C" of Example III.

EXAMPLE X

A culture medium is prepared as in Example I using agar and pectin as the gelling agent; 1,3-dichloro-5,5-dimethylhydantoin as the sterilizing agent, sodium thiosulfate as the halogen-inactivating agent and packet "C" of Example III.

EXAMPLE XI

A culture medium is prepared as in Example III using guar gum as the gelling agent n-bromo-n-chlorosulfamyl benzoic acid as the sterilizing agent, sodium thioglycollate as the halogen-inactivating agent and packet "C" of Example II.

EXAMPLE XII

A culture medium is prepared as in Example II using agar, bromine chloride as the sterilizing agent, sodium thiosulfate as the halogen-inactivating agent and packet "C" of Example II.

EXAMPLE XIII

A culture medium is prepared as in Example IV using benzalkonium chloride as the sterilizing agent, agar agar as the gelling agent, sodium thioglycollate as the germicide-inactivating agent and packet "C" of Example III.

The medium of this invention is instantly ready to pour or if desired, 50 c.c. of fresh and sterile defibrinated sheep or horse blood can be added taking sterile precautions, mixed well and the nutrient blood agar medium is ready for pouring. There is no need to wait for the medium to cool, as its temperature is already controlled.

The medium of this invention typically sets (solidifies) promptly, because of its controlled temperature and will not cause excessive moisture on the lid or walls of the containers (Petri dishes or tubes, etc.). The surface of the medium is bubble free. The medium will grow distinctly better all micro-organisms that grow on blood agar with the highest recovery rate attainable and with the easiest-to-read reactions, e.g. hemolysis, morphology, size of the colonies, etc. All the above mentioned drawbacks inherent in heat sterilization are completely avoided.

The medium of the invention has been thoroughly tested under actual use conditions and has been found to be completely successful for the accomplishment of the above stated objects of the invention. It was also observed that the Instant Blood Agar for example displays remarkable chromogenic activity not displayed by the heat-sterilized blood agar.

The present invention has been disclosed herein with particular respect to certain preferred embodiments thereof. However, a latitude of modification, change and substitution is intended in the foregoing disclosure, and in some instances some components of the invention will be employed with certain other components for optimum results. Accordingly, other compositions encompassed by the above disclosure are fully equivalent to those claimed hereinbelow.

What is claimed is:

1. A culture medium comprising in weight percent:
   about 0.00 to 5% of a gelling agent;
   about 0.015 to 0.03% of a bleaching agent having germicidal and biocidal properties and containing at least one halogen or halogen-liberating compound capable of providing a final halogen concentration in water of about 50 to 100 parts per million;
   about 0.22 to 0.06% of a halogen-inactivating agent having at least one thio, mercapto or sulfhydril group
   about 7 to 50% of a nutrient; balance, water.

2. The culture medium of claim 1, wherein said bleaching agent is selected from the group of chlorine, iodine, bromine, sodium hypochlorite, calcium hypochlorite, lithium hypochlorite, sodium and potassium dichloro-s-triazinetrione; N-chloro-N-bromo-5,5-dimethylhydantoin, 1,3-dichloro-5,5-dimethyldantoin, p-(N,N-dichloro sulfamyl) benzoic acid; trichloro-s-triazinetrione; bromine chloride, iodine chloride, iodine bromide, benzalkonium chloride and mixtures thereof.

3. The medium of claim 1, wherein said halogen-inactivating agent is selected from the group of sodium thiosulfate, sodium bisulfite and sodium thioglycollate.

4. The medium of claim 1, wherein said gelling agent is agar agar, carrageenan, pectin, silicone gel, guar gum, locust bean gum, corn starch, alginic acid, kelp and mixtures thereof.

5. The medium of claim 1, wherein said water is distilled water or demineralized water.

6. The medium of claim 1, wherein said nutrient is sterilized or presterilized.

7. A method for forming and sterilizing a culture medium which comprises providing in a culture medium container at least one soluble biocidal and germicidal agent containing at least one halogen or halogen-liberating compound; adding thereto a halogen inactivating agent having at least one thio, mercapto or sulfhydril group in an amount sufficient to inactivate any residual halogen and then adding to the container contents a sterilized nutrient concentrate.

8. The method of claim 7, wherein said bleaching agent is a quaternary ammonium halide or hyamine salt and said neutralizing agent is sodium thioglycolate.

9. The method of claim 7, wherein said bleaching agent is an aldehyde and said neutralized agent is an oxidizing substance used with buffing salts.

10. The method of claim 9, wherein said aldehyde is formaldehyde or a derivative thereof and said oxidizing substance is an alkali metal persulfate.

* * * * *